US00PP12084P2

(12) United States Plant Patent
Kaerwer et al.

(10) Patent No.: US PP12,084 P2
(45) Date of Patent: Sep. 11, 2001

(54) BERMUDA GRASS 'P18'

(76) Inventors: Howard E. Kaerwer, *deceased*, late of Eden Prairie, MN (US); by Barbara Kaerwer, executer, 12800 Gerard Dr., Eden Prairie, MN (US) 55346

( * ) Notice: Subject to any disclaimer, the term of this patent is extended or adjusted under 35 U.S.C. 154(b) by 0 days.

(21) Appl. No.: 09/386,225

(22) Filed: Aug. 31, 1999

(51) Int. Cl.[7] ..... A01H 5/00
(52) U.S. Cl. ..... Plt./389

(58) Field of Search ..... Plt./389

*Primary Examiner*—Bruce R. Campell
*Assistant Examiner*—Annette H. Para
(74) *Attorney, Agent, or Firm*—Rothwell, Figg, Ernst & Manbeck

(57) ABSTRACT

This invention relates to a new and distinct Bermudagrass (*Cynodon dactylon*) designated P-18 which is outstanding because of its 1) extremely fine leaves; 2) its improved density; 3) its rapid growth rate; and 4) its uniform green color.

6 Drawing Sheets

Bermudagrass (*Cynodon dactylon* (L.)) 'P-18' is a new and distinct cultivar of turfgrass which is developed for golf greens, tees, fairways, athletic fields and home lawn grass.

BACKGROUND

An important characteristic of a good turfgrass is density. Maintaining good density at very low heights is particularly vital when used one golf course greens which are typically maintained at a height of 1/18 inch. At this height, density is critical to avoid sunlight from reaching the surface of the soil. When this happens, weed invasion becomes more a problem but most greens receive a daily irrigation which allows algae to begin to grow on the soil. Algae causes the turf to lose even more density creating thinning or even bare spots on the greens.

In order to accommodate the low mowing heights on a putting green, it is desirable to have a variety which exhibits a fine leaf texture and a vertical leaf orientation. Due to frequent mowing, leaves which grow vertical are beneficial in providing a flat surface for golfing.

Turfgrass varieties selected for putting greens must have quality characteristics of: 1) density; 2) low, creeping growth habit; 3) tolerance to close mowing; 4) fine leaf texture; 5) excellent reproduction rate; and 6) good uniform color.

SUMMARY OF THE INVENTION

This invention relates to a new and distinct Bermudagrass (*Cynodon dactylon*) designated P-18 which is outstanding because of its 1) extremely fine leaves; 2) its improved density; 3) its rapid growth rate; and 4) its uniform green color. The claimed Bermudagrass P18 was primarily selected for these characteristics. This selection was made from a breeding program designed to develop improved varieties of seed producing Bermudagrass in Yuma, Ariz.

ORGIN AND ASEXUAL REPRODUCTION

Asexual reproduction of this turfgrass by vegetative propagation was directed by me, such reproduction establishing that the plant does in fact maintain the characteristics described, in successive generations. 'P-18' was first produced in 1992 and is a mutant obtained from a Bermuda line believed to be TifDwarf Bermuda grass which was grown in a greenhouse owned by H&H Seed Company in Yuma, Ariz. 'P-18' was selected and evaluated for traits and characteristics as described in the patent application. 'P-18' has been asexually reproduced for several generations and the traits have been stable.

BRIEF DESCRIPTION OF THE DRAWING

The accompanying photograph show as nearly true as it is reasonably possible to make the same, in color illustrations of this character, the new variety.

DETAILED DESCRIPTION OF THE INVENTION

Figure 1:
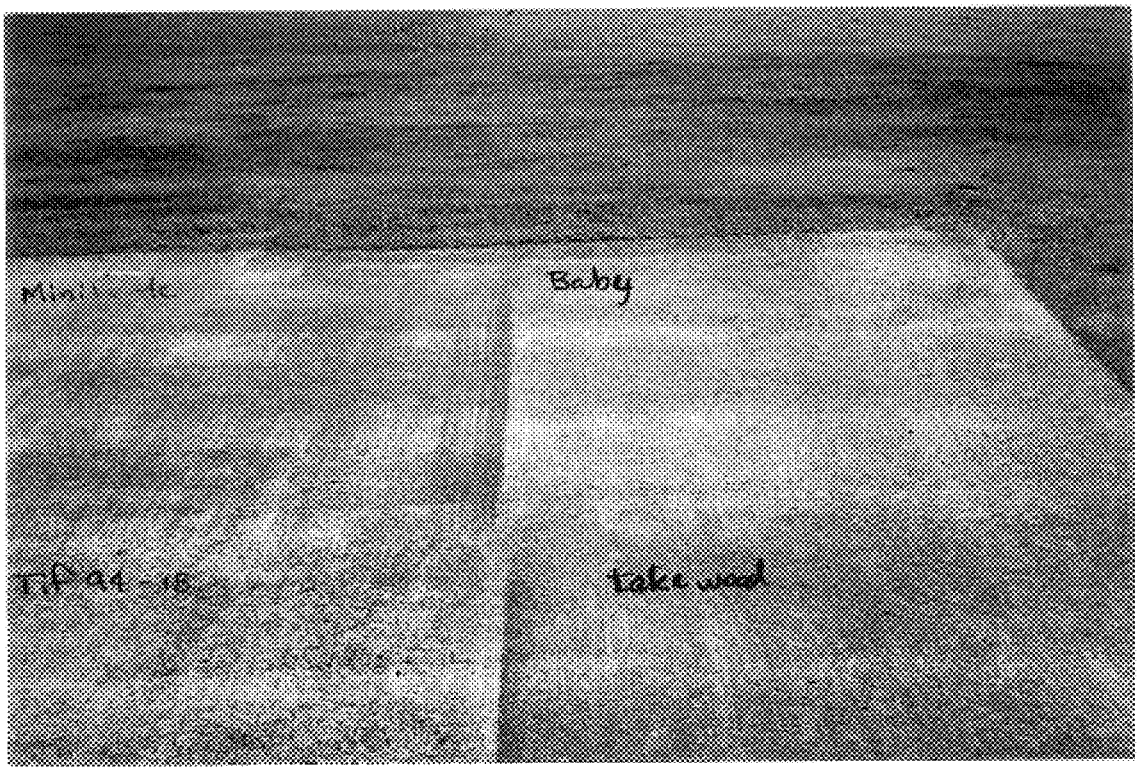
FIG. 1 shows P-18 (Mini-Verde™) growing in a field trial along with Baby Bermuda, Tif 94-18 and Lakewood Bermuda. Tif 94-18 and Lakewood Bermuda were experimental cultivars in this study. The greens were topdressed with sand prior to the photo being taken. Turf quality is apparent and indicated by color and density.
Figure 2:
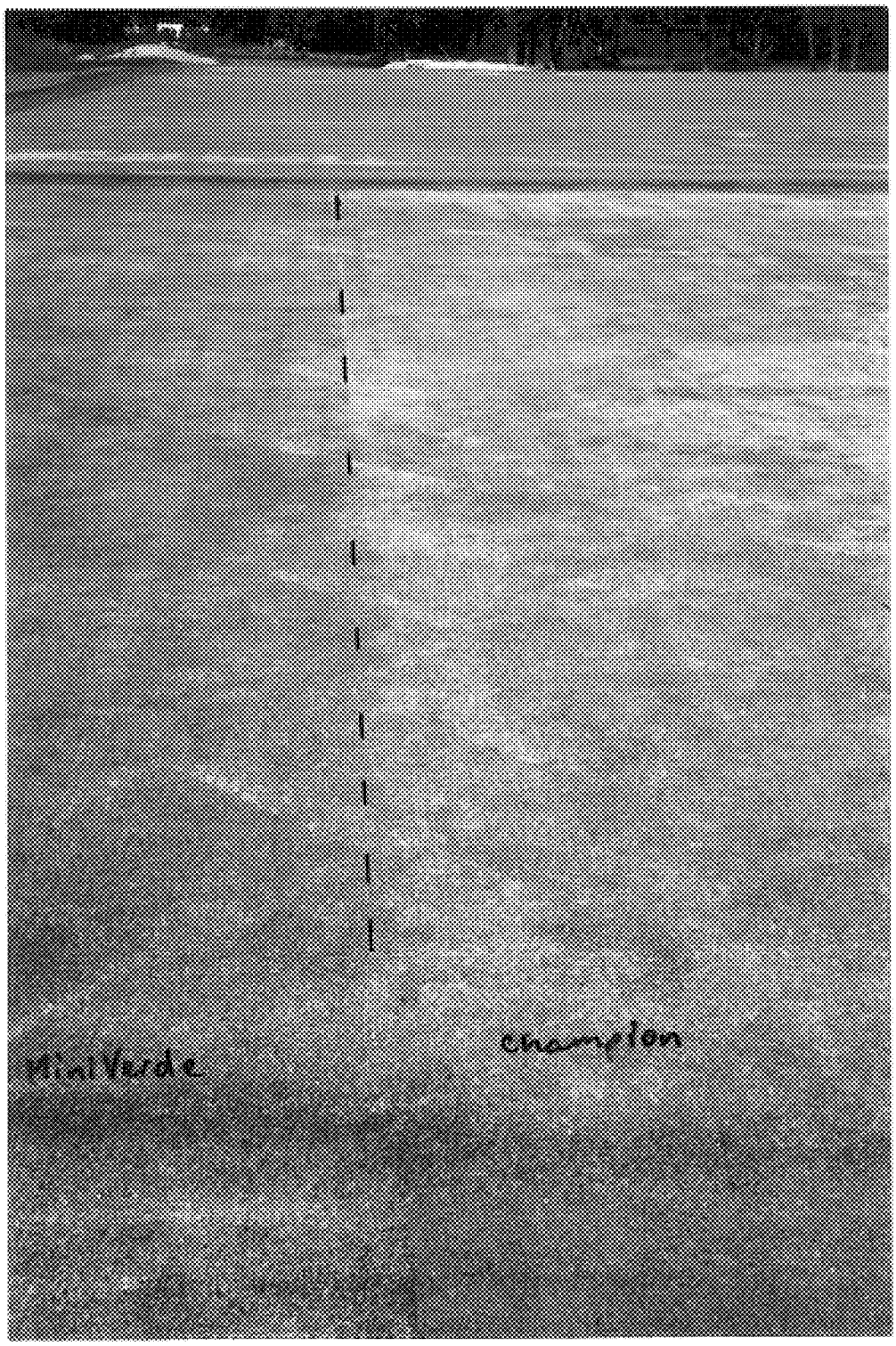
FIG. 2 shows P-18 beside Champion bermudagrass. The discolored and bare areas in the Champion side are from disease pressure. The mower scalp marks in the P-18 side are from areas of high fertility treatment.
Figure 3:
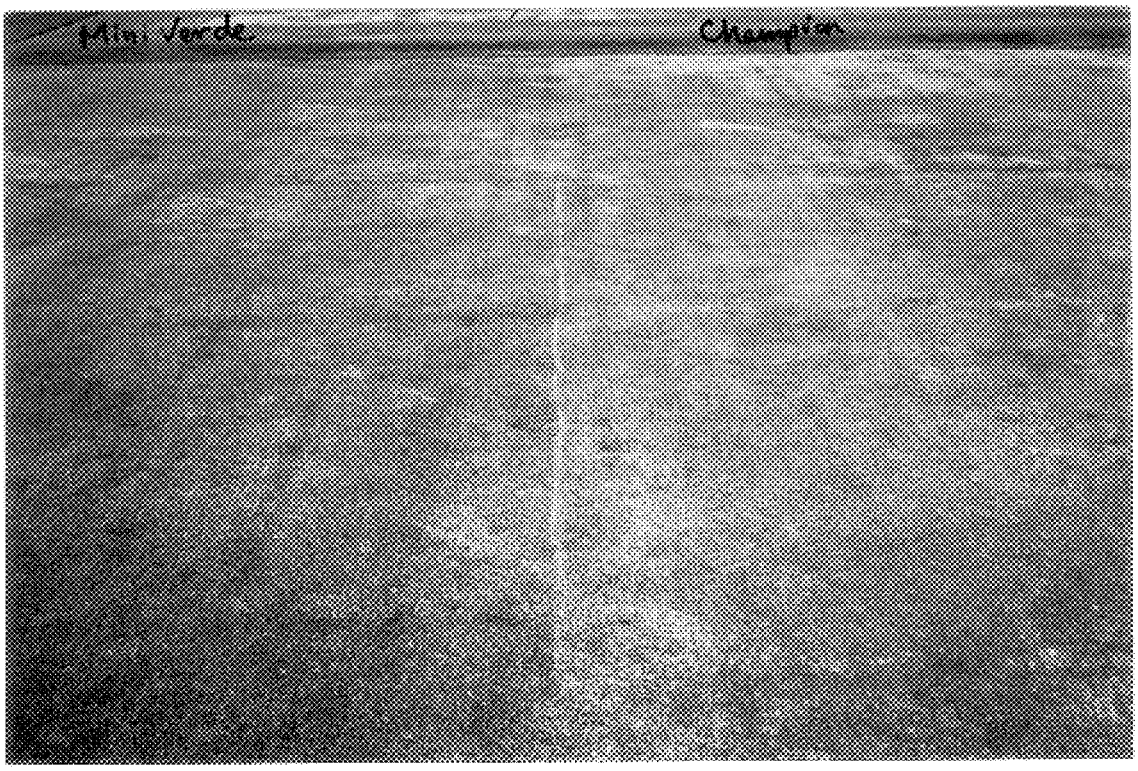
FIG. 3 shows P-18 beside Champion bermudagrass. Lines in the turf are from vertical mowing and P-18 shows less damage from this treatment.
Figure 4:
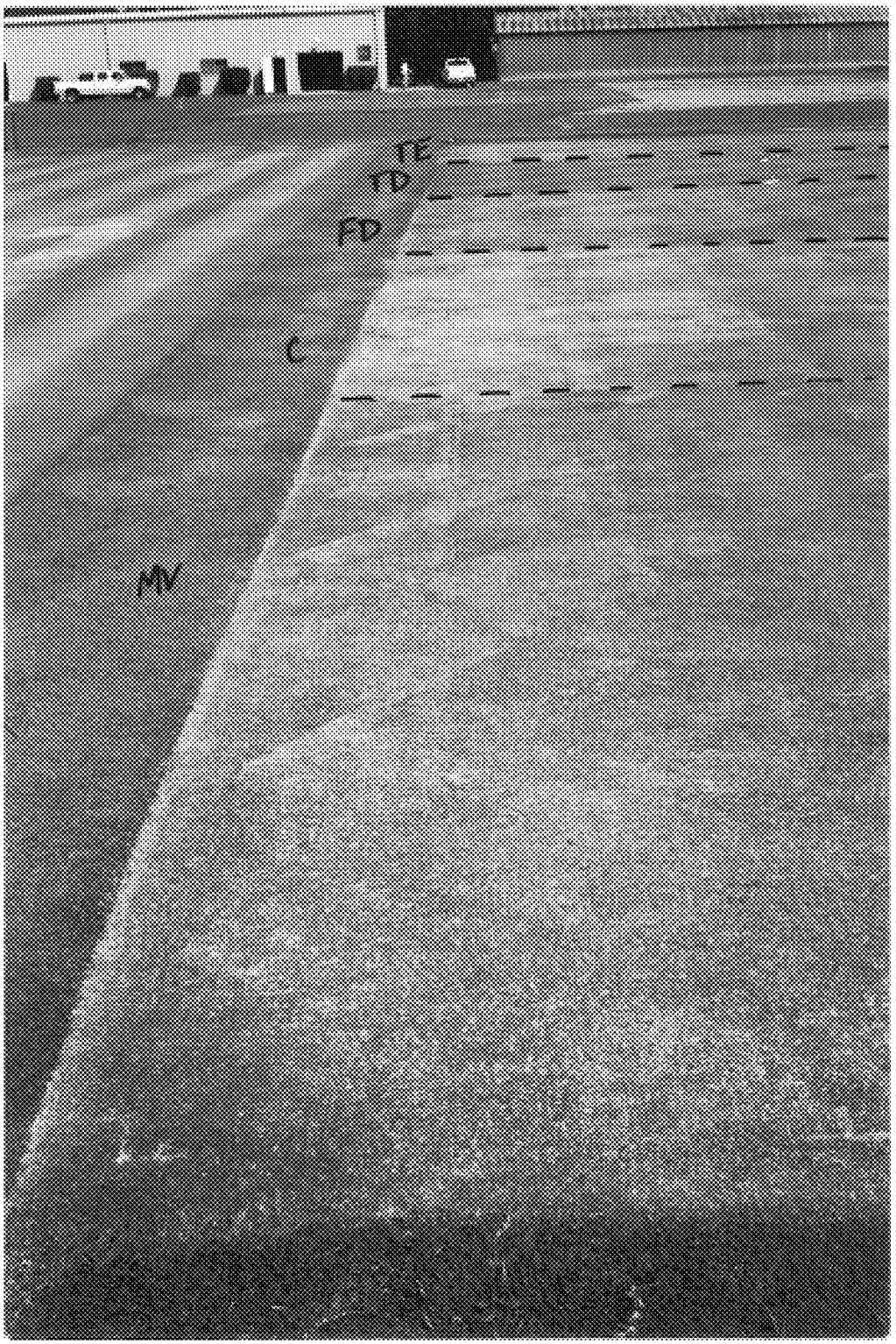
FIG. 4 shows all entries in the trial. MV=P-18, C=Champion, FD=Floradwarf, TD=Tifdrawf and TE=TidEagle. Disease pressure is noted in Champion, Floradwarf and TifEagle.
Figure 5:
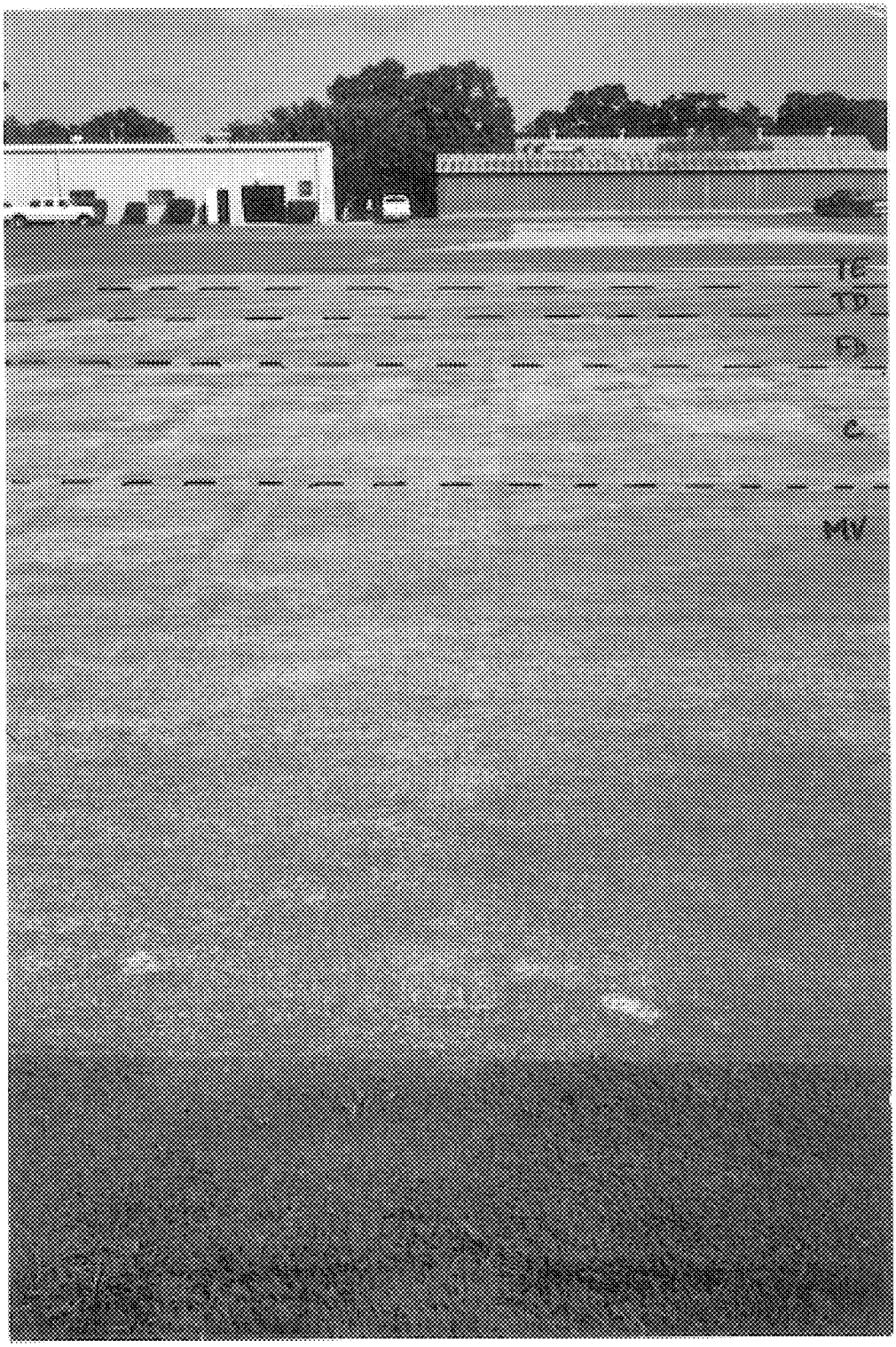
FIG. 5 shows the middle of the plot design to exhibit turf quality and genetic color. MV=P-18, C=Champion, FD=Floradwarf, TD=Tifdwarf and TE=TifEagle.
Figure 6:
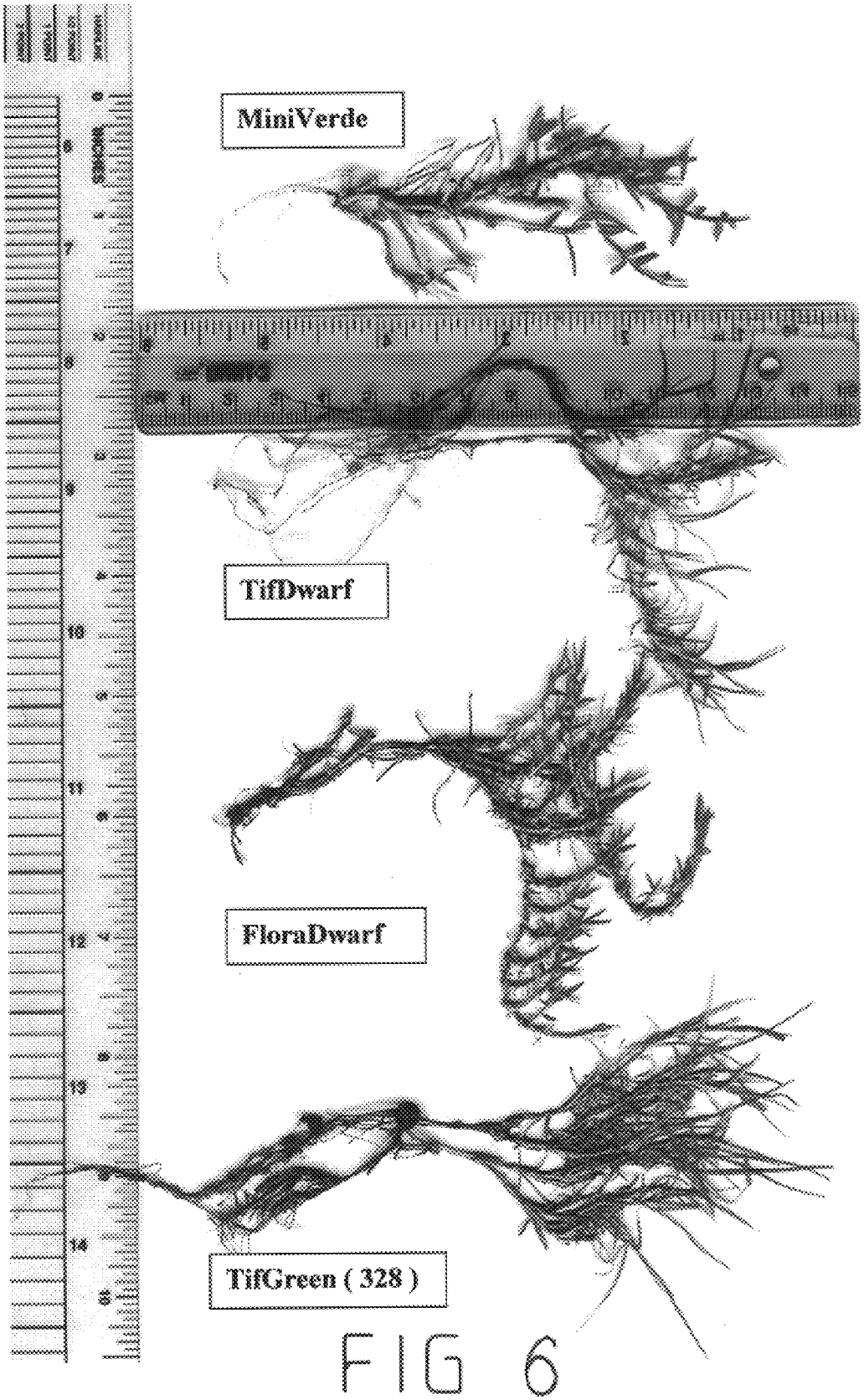
FIG. 6 shows P-18 (MiniVerde), Tifdwarf, Floradwarf and Tifgreen in a close-up side-by-side comparison showing root structure and fine leaf texture.

Parentage: Unknown.

*Morphological characteristics observed.*—a) Reproduction was vegetative with no seedheads observed. b) Leaves were flattened and V-shaped, with a prominent midrib and tip tapering to an acute point.

c) Upper leaf surface is sparsely pubescent. d) Lower leaf surface is glabrous. e) Leaf edge is smooth. f) Venation is folded in the bud shoot. g) Leaf sheath is open, rounded, split, and glabrous. h) Collar is narrow and continuous. i) Ligule is pubescent with fringe-of-hair.

*Assessment of the* 3.2 *mm cutting height.*—a) Mean shoot/leaf vertical extension rate was 0.7 mm/day. b) mean number of stolons extending exterior to the pot rim was 48 per linear 100-mm and mean stolon length was 11 mm. c) Mean visual turfgrass quality was 6.0, using the 1 to 9 scale with 1 equaling poorest. d) Mean internode length of the 2nd youngest internode was 2.1 mm. e) Mean turf color assessed using The R.H.S. chart reference was medium light green RHS 138A. f) Mean leaf blade width of youngest fully expanded leaf was 1 mm. g) Mean mat biomass depth was 28 mm. h) Mean root length of longest intact root was 123 mm. i) Mean shoot density was 2,735 $dm^2$.

*Assessment of the* 6.4 *mm cutting height.*—a) Mean shoot/leaf vertical extension rate was 2.1 mm/day. b) Mean number of stolons extending exterior to the pot rim was 58 per linear 100-mm and mean stolon length was 14 mm. c) Mean visual turfgrass quality was 6.0, using the 1 to 9 scale with 1 equaling poorest. d) Mean internode length of the 2nd youngest internode was 3 mm. e) Mean turf color assessed using The R.H.S. chart reference was medium light green RHS 138A. f) Mean leaf blade width was 1.4 mm. g) Mean mat biomass depth was 19 mm. h) Mean root length of longest intact root was 105 mm. i) Mean shoot density was 938 $dm^2$.

*Assessment of the unmowed replications after* 3 *months growth.*—a) Mean shoot/leaf vertical extension rate was 34 mm. b) Mean number of stolons extending exterior to the pot rim was 68 per linear 100-mm and mean stolon length was 197 mm. c) Mean visual turfgrass quality was 5.3, using the 1 to 9 scale with 1 equaling poorest. d) Mean internode length of the 2nd youngest internode was 9 mm; stolen internode length was 12 to 15 mm. e) Mean turf color assessed using The R.H.S. chart reference was medium light green RHS 137B. f) Mean leaf blade width was 1.5 mm. g) Mean mat biomass depth was 28 mm. h) Mean root length of longest intact root was 115 mm. i) Mean shoot density was 438 $dm^2$. j) Mean unmowed terminal shoot height was 34 mm.

TABLES

Listed below are several tables which compare the claimed variety, P-18, now being marked under "Mini-Verde™". These tables were taken from the "On-Site Evaluation of Bermudagrass for Putting Greens—Progress Report 1998" which is sponsored by the National Turfgrass Evaluation Program, United States Golf Association and the Golf Course Superintendents Association of America which is published by the National Turfgrass Federation, Inc. of the United States Department of Agriculture, Beltsville, Md. 20705. The age of the grass from this test is two years old in a golf course setting.

Definitions: In the description and tables which follow, a number of terms are used. In order to provide a clear and consistent understanding of the specification and claim, including the scope to be given such terms, the following definitions are provided:

*Genetic color.*—Genetic color reflects the inherent color of the genotype. It is based on a visual rating scale with 1 being light green and 9 being dark green. Genetic color ratings are collected when the turf is actively growing and is not under stress. Chlorosis and browning from necrosis are not a part of genetic color.

*Winter color.*—Winter color is an assessment of color retention during the winter months. It is based on a 1 to 9 visual rating scale with 1 equaling straw brown or no color retention, and 9 equaling dark green. It assesses overall plot color and not genetic color.

*Seasonal color/color retention.*—Seasonal color and color retention ratings are a measure of overall plot color. The scale used is 1 to 9 scale with 1 being straw brown and 9 being dark green. Seasonal color can be used to successfully differentiate color differences based on damage caused by disease or insect pests, nutrient deficiency or environmental stress. Color retention is used to assess the ability of the entry to hold color as seasons change. This is especially useful in quantifying the response of warm-season grasses to temperature changes or frost occurring in fall.

*Quality.*—Quality is based on 9 being outstanding or ideal turf and 1 being poorest or dead. A rating of 6 or above is generally considered acceptable. A quality rating value of 9 is reserved for a perfect or ideal grass, but it also can reflect an absolutely outstanding treatment plot. The NTEP requires quality ratings on a monthly basis.

Quality ratings will vary based on turfgrass species, intensity of management and time of year. Within species, quality ratings are relative. Among species, they are not. For example, an acceptable quality rating of 6 within tall fescue cultivars is not relative to the same value given among Kentucky bluegrasses. An acceptable quality rating value for a utility turf differs from the same value for a bentgrass putting green.

Quality ratings take into account the aesthetic and functional aspects of the turf. Quality ratings are not based on color alone, but on a combination of color, density, uniformity, texture, and disease or environmental stress. Turfs growing in a study may receive the same numeric quality rating, but the factors influencing that rating may differ. For example, one turf may receive a quality rating value of 5 based on overall color and density, while another may receive the same value based on disease incidence and its impact on turfgrass density.

Table 1 shows the results of a test conducted by the USGA/GCSAA/NTEP Trials at the Country Club of Birmingham in Birmingham, Ala. In Table 1 Floradwarf, P-18, and MS-Supreme are similar in this trial. There are no significant differences between the three above-mentioned varieties in this test.

Table 2 shows the results of a test conducted by the USGA/GCSAA/NTEP on-site at the Country Club of Mobile in Mobile, Ala. P-18 has a better quality rating than MS-Supreme and Floradwarf during September, October and November.

Table 3 shows the results of a test conducted by the USGA/GCSAA/NTEP on-site at the Country Club of Green Valley in Green Valley, Ariz. P-18 did not perform as well on this trial. P-18 may be better adapted to Southern climates in Southern parts of the United States and Texas.

Table 4 shows the results of a test conducted by the USGA/GCSAA/NTEP on-site at the Jupiter Island Club in Hobe Sound, Fla. P-18 was superior in all of the tests conducted at this site. This table shows that P-18 has a higher rating in color and leaf texture.

Table 5 shows the results of a test conducted by the USGA/GCSAA/NTEP on-site test at the Bent Tree Country Club in Dallas, Tex. P-18 was superior to all other entries and had a genetic color mean of 7.7.

Table 6 shows the results of a test conducted by the USGA/GCSAA/NTEP on-site at the Lakeside Country Club in Houston, Tex. P-18 was at the top of the trials in August, September and October, outperforming all other comparisons.

TABLE 1

Mean Turfgrass Quality and Other Ratings of Bermudagrass Cultivars in the 1998 USGA/GCSAA/NTEP On-Site Bermudagrass Test at Birmingham, AL (Country Club of Birmingham) 1998 Data Turfgrass Quality and Other Ratings 1–9; 9 = Best

| Name | % Establish. 5 Weeks | Overseed OCT | Establish. NOV |
|---|---|---|---|
| Floradwarf | 65.0 | 4.0 | 3.0 |
| P-18 | 61.7 | 4.7 | 3.3 |
| MS-Supreme | 71.7 | 4.0 | 2.7 |
| Tifeagle | 58.3 | 4.7 | 2.7 |
| Champion | 60.0 | 4.3 | 3.0 |
| Tifdwarf | 71.7 | 4.7 | 3.0 |
| Tifgreen | 76.7 | 2.3 | 2.3 |
| LSD Value | 14.2 | 1.5 | |
| C.V. (%) | 10.5 | 18.6 | 19.7 |

| | Color Ratings | | | |
|---|---|---|---|---|
| Name | JUN | JUL | AUG | SEP |
| Floradwarf | 7.0 | 6.3 | 6.7 | 7.0 |
| P-18 | 6.7 | 6.0 | 6.7 | 5.7 |
| MS-Supreme | 6.7 | 5.3 | 6.0 | 6.0 |
| Tifeagle | 6.3 | 6.7 | 6.3 | 6.3 |
| Champion | 7.0 | 6.0 | 6.3 | 5.0 |
| Tifdwarf | 6.0 | 5.7 | 6.0 | 4.3 |
| Tifgreen | 6.0 | 4.7 | 3.7 | 2.0 |
| LSD Value | 0.7 | 1.3 | 0.9 | 1.2 |
| C.V. (%) | 5.6 | 11.6 | 8.8 | 13.5 |

| | Quality Ratings | | | | |
|---|---|---|---|---|---|
| Name | JUN | JUL | AUG | SEP | Mean |
| Floradwarf | 7.0 | 5.3 | 5.0 | 7.7 | 6.3 |
| P-18 | 6.7 | 4.7 | 6.7 | 6.7 | 6.2 |
| MS-Supreme | 6.7 | 5.3 | 6.0 | 6.7 | 6.2 |
| Tifeagle | 6.3 | 4.3 | 5.7 | 7.0 | 5.8 |
| Champion | 6.3 | 5.0 | 5.3 | 6.0 | 5.7 |
| Tifdwarf | 6.3 | 5.0 | 5.3 | 5.0 | 5.4 |
| Tifgreen | 6.0 | 4.3 | 3.7 | 3.0 | 4.3 |
| LSD Value | 1.1 | | 1.2 | 1.4 | 0.6 |
| C.V. (%) | 7.3 | 13.4 | 11.9 | 13.6 | 6.4 |

1/To determine statistical differences among entries, subtract one entry's mean from another entry's mean. Statistical differences occur when this value is larger than the corresponding LSD value (LSD 0.05).
2/C.V. (Co-efficient of variation) indicates the percent variation of the mean in each column.

TABLE 2

Mean Turfgrass Quality and Other Ratings of Bermudagrass Culitvars in the 1998 USGA/GCSAA/NTEP On-Site Bermudagrass Test at Mobile, AL (Country Club of Mobile) 1998 Data Turfgrass Quality and Other Ratings 1–9; 9 = Best

| | Leaf | Establish. | Quality Ratings | | | |
|---|---|---|---|---|---|---|
| Name | Texture | Rat'g | SEP | OCT | NOV | MEAN |
| P-18 | 9 | 5.3 | 8.5 | 8.3 | 8.0 | 8.3 |
| MS-Supreme | 9 | 5.5 | 8.3 | 8.0 | 8.0 | 8.1 |
| Flordawarf | 9 | 5.3 | 8.0 | 7.8 | 8.0 | 7.9 |
| champion | 9 | 5.5 | 7.5 | 7.8 | 7.8 | 7.7 |
| Tifeagle | 9 | 5.8 | 7.3 | 7.5 | 7.5 | 7.4 |
| Tifdwarf | 9 | 5.8 | 6.5 | 6.8 | 6.8 | 6.7 |
| Tifgreen | 7 | 5.8 | 6.8 | 6.8 | 6.5 | 6.7 |
| LSD Value | 0 | | 0.7 | 0.6 | 0.6 | 0.5 |
| C.V. (%) | 0 | 14.0 | 6.3 | 5.9 | 5.8 | 4.7 |

1/To determine statistical differences among entries, subtract one entry's mean from another entry's mean. Statistical differences occur when this value is larger than the corresponding LSD value (LSD 0.05).
2/C.V. (Co-efficient of variation) indicates the percent variation of the mean in each column.

TABLE 3

Mean Turfgrass Quality and Other Ratings of Bermudagrass Culitvars in the 1998 USGA/GCSAA/NTEP On-Site Bermudagrass Test at Green Valley, AZ (Country Club of Green Valley) 1998 Data Turfgrass Quality and Other Ratings 1–9; 9 = Best

| | | | | Density Rating | |
|---|---|---|---|---|---|
| Name | Genetic Color | Leaf Texture | Estab. Rating | Sum-mer | Fall |
| Tifgreen | 8.0 | 7.3 | 6.3 | 5.3 | 7.3 |
| Tifeagle | 8.0 | 8.0 | 6.3 | 5.3 | 7.0 |
| Tifdwarf | 7.7 | 8.0 | 6.7 | 5.7 | 7.7 |
| MS-Supreme | 7.7 | 8.0 | 5.3 | 4.3 | 6.3 |
| Champion | 7.7 | 8.7 | 5.7 | 4.7 | 7.0 |
| Floradwarf | 6.0 | 6.0 | 8.7 | 7.7 | 8.3 |
| P-18 | 8.3 | 9.0 | 5.0 | 4.0 | 6.3 |
| LSD Value | 1.4 | 0.9 | 0.9 | 1.0 | 0.9 |
| C.V. (%) | 9.5 | 6.4 | 8.9 | 10.9 | 7.1 |

| | % Estab. Ratings | | Quality Ratings | | |
|---|---|---|---|---|---|
| Name | Sum-mer | Fall | OCT | NOV | MEAN |
| Tifgreen | 53.3 | 86.0 | 7.3 | 7.3 | 7.3 |
| Tifeagle | 50.0 | 83.3 | 8.0 | 6.3 | 7.2 |
| Tifdwarf | 55.0 | 86.0 | 8.0 | 6.0 | 7.0 |
| MS-Supreme | 43.3 | 80.3 | 7.3 | 6.0 | 6.7 |
| Champion | 43.3 | 81.0 | 7.7 | 5.3 | 6.5 |
| Floradwarf | 75.0 | 94.7 | 5.3 | 7.0 | 6.2 |
| P-18 | 40.0 | 76.0 | 6.7 | 5.0 | 5.8 |
| LSD Value | 8.3 | 5.8 | 1.4 | 1.0 | 1.2 |
| C.V.(%) | 9.6 | 3.9 | 10.6 | 9.4 | 8.9 |

1/To determine statistical differences among entries, subtract one entry's mean from another entry's mean. Statistical differences occur when this value is larger than the corresponding LSD value (LSD 0.05).
2/C.V. (Co-efficient of variation) indicates the percent variation of the mean in each column.

TABLE 4

Mean Turfgrass Quality and Other Ratings of Bermudagrass Culitvars in the 1998 USGA/GCSAA/NTEP On-Site Bermudagrass Test at Hobe Sound, FL (The Jupiter Island Club)
1998 Data
Turfgrass Quality and Other Ratings 1–9; 9 = Best

| Name | Genetic Color | Leaf Texture | Density Fall | Stimpmeter Readings |
|---|---|---|---|---|
| P-18 | 8.7 | 8.7 | 8.7 | 91.0 |
| Flordawarf | 7.3 | 7.3 | 7.0 | 104.7 |
| Tifeagle | 7.7 | 7.7 | 7.0 | 89.3 |
| Champion | 7.7 | 8.0 | 7.3 | 94.7 |
| Tifdwarf | 7.0 | 6.0 | 6.7 | 92.0 |
| MS-Supreme | 6.0 | 6.7 | 5.3 | 89.7 |
| Tifgreen | 5.3 | 4.3 | 4.3 | 81.7 |
| LSD Value | 0.9 | 1.4 | 0.8 | 16.8 |
| C.V. (%) | 7.3 | 11.6 | 7.1 | 8.6 |

| | % Establishment Ratings | | | | |
|---|---|---|---|---|---|
| Name | 7/14 | 8/01 | 8/14 | 8/29 | 9/26 |
| P-18 | 31.7 | 60.0 | 85.0 | 96.3 | 99 |
| Flordawarf | 31.7 | 55.0 | 86.7 | 99.0 | 99 |
| Tifeagle | 40.0 | 65.0 | 85.0 | 94.3 | 99 |
| Champion | 40.0 | 63.3 | 81.7 | 97.0 | 99 |
| Tifdwarf | 25.0 | 53.3 | 80.0 | 96.0 | 99 |
| MS-Supreme | 43.3 | 68.3 | 91.3 | 98.3 | 99 |
| Tifgreen | 38.3 | 85.0 | 97.7 | 99.0 | 99 |
| LSD Value | 18.2 | 21.2 | 8.2 | 4.6 | |
| C.V. (%) | 23.1 | 16.3 | 5.1 | 2.2 | |

| | Quality Ratings | | | | |
|---|---|---|---|---|---|
| Name | SEP | OCT | NOV | DEC | MEAN |
| P-18 | 9.0 | 7.0 | 8.7 | 8.0 | 8.2 |
| Flordawarf | 8.7 | 7.7 | 7.3 | 6.7 | 7.6 |
| Tifeagle | 8.0 | 7.0 | 7.3 | 8.0 | 7.6 |
| Champion | 7.3 | 6.0 | 7.0 | 8.7 | 7.3 |
| Tifdwarf | 8.0 | 6.3 | 7.3 | 5.7 | 6.8 |
| MS-Supreme | 6.7 | 5.3 | 6.3 | 7.0 | 6.3 |
| Tifgreen | 4.0 | 3.0 | 4.7 | 3.7 | 3.8 |
| LSD Value | 0.9 | 1.7 | 1.2 | 1.2 | 0.6 |
| C.V. (%) | 7.1 | 15.7 | 9.8 | 10.9 | 5.4 |

1/To determine statistical differences among entries, subtract one entry's mean from another entry's mean. Statistical differences occur when this value is larger than the corresponding LSD value (LSD 0.05).
2/C.V. (Co-efficient of variation) indicates the percent variation of the mean in each column.

TABLE 5

Mean Turfgrass Quality and Other Ratings of Bermudagrass Culitvars in the 1998 USGA/GCSAA/NTEP On-Site Bermudagrass Test at Dallas, TX (Bent Tree Country Club)
1998 Data
Turfgrass Quality and Other Ratings 1–9; 9 = Best

| Name | Genetic Color | Winter Color | 1 Week | 5 Weeks | 8 Weeks |
|---|---|---|---|---|---|
| P-18 | 7.7 | 8.0 | 66.7 | 40.0 | 53.3 |
| Tifeagle | 7.3 | 7.7 | 88.3 | 53.3 | 36.7 |
| Flordawarf | 8.7 | 7.3 | 66.7 | 58.3 | 63.3 |
| Tifdwarf | 7.7 | 5.3 | 76.7 | 40.0 | 26.7 |
| Champion | 6.7 | 7.7 | 91.7 | 33.3 | 23.3 |
| MS-Supreme | 7.3 | 7.0 | 73.3 | 53.3 | 80.0 |
| Tifgreen | 6.3 | 3.7 | 85.0 | 70.0 | 80.0 |

TABLE 5-continued

Mean Turfgrass Quality and Other Ratings of Bermudagrass Culitvars in the 1998 USGA/GCSAA/NTEP On-Site Bermudagrass Test at Dallas, TX (Bent Tree Country Club)
1998 Data
Turfgrass Quality and Other Ratings 1–9; 9 = Best

| | | | | | |
|---|---|---|---|---|---|
| LSD Value | 1.7 | 1.0 | 22.0 | 19.4 | 19.2 |
| C.V. (%) | 10.9 | 9.4 | 13.6 | 20.6 | 21.7 |

| | Quality Ratings | | | | |
|---|---|---|---|---|---|
| Name | SEP | OCT | NOV | DEC | MEAN |
| P-18 | 8.3 | 7.0 | 7.7 | 7.7 | 7.7 |
| Tifeagle | 6.7 | 7.7 | 7.7 | 7.0 | 7.3 |
| Flordawarf | 7.7 | 7.0 | 7.0 | 6.7 | 7.1 |
| Tifdwarf | 7.0 | 6.7 | 6.7 | 6.0 | 6.6 |
| Champion | 5.7 | 6.3 | 6.3 | 7.0 | 6.3 |
| MS-Supreme | 7.3 | 6.0 | 6.0 | 6.0 | 6.3 |
| Tifgreen | 6.0 | 5.7 | 6.0 | 5.0 | 5.7 |
| LSD Value | 1.4 | 0.8 | 0.7 | 1.1 | 0.5 |
| C.V. (%) | 10.5 | 6.6 | 6.0 | 9.6 | 4.6 |

1/To determine statistical differences among entries, subtract one entry's mean from another entry's mean. Statistical differences occur when this value is larger than the corresponding LSD value (LSD 0.05).
2/C.V. (Co-efficient of variation) indicates the percent variation of the mean in each column.

TABLE 6

Mean Turfgrass Quality and Other Ratings of Bermudagrass Cultivars in the 1998 USGA/GCSAA/NTEP On-Site Bermudagrass Test at Houston, TX (Lakeside Country Club)
1998 Data
Turfgrass Quality and Other Ratings 1–9; 9 = Best

| | Genetic | Establishment | Quality Ratings | | | |
|---|---|---|---|---|---|---|
| Name | Color | Rating | AUG | SEP | OCT | MEAN |
| P-18 | 5.0 | 7.0 | 5.0 | 5.7 | 5.7 | 5.4 |
| Champion | 4.3 | 6.0 | 5.0 | 5.7 | 5.3 | 5.3 |
| Floradwarf | 4.7 | 6.3 | 4.0 | 4.7 | 5.7 | 4.8 |
| MS-Supreme | 3.3 | 7.3 | 3.7 | 5.0 | 5.7 | 4.8 |
| Tifeagle | 3.0 | 6.3 | 3.3 | 4.7 | 6.0 | 4.7 |
| Tifdwarf | 3.3 | 7.0 | 2.3 | 3.3 | 5.0 | 3.6 |
| Tifgreen | 1.0 | 7.3 | 1.0 | 1.0 | 1.0 | 1.0 |
| LSD Value | 1.9 | 0.8 | 1.6 | 1.3 | 1.1 | 1.2 |
| C.V. (%) | 28.4 | 6.6 | 26.1 | 17.5 | 13.0 | 17.3 |

1/To determine statistical differences among entries, subtract one entry's mean from another entry's mean. Statistical differences occur when this value is larger than the corresponding LSD value (LSD 0.05).
2/C.V. (Co-efficient of variation) indicates the percent variation of the mean in each column.

COMPARISON WITH KNOWN CULTIVAR

A similar Bermudagrass to P-18 would be Tifdwarf. P-18 has consistently better color ratings, quality ratings, and density ratings when compared to Tifdwarf. Additionally, P-18 has a significantly shorter root structure than Tifdwarf.

I claim:

1. A new and distinct Bermudagrass plant named 'P-18', substantially as herein shown and described.

* * * * *